United States Patent [19]

Cirincione

[11] Patent Number: 4,459,864
[45] Date of Patent: Jul. 17, 1984

[54] FLUID LOADING AND DISPENSING DEVICE

[75] Inventor: Thomas J. Cirincione, Flushing, N.Y.

[73] Assignee: Electro-Nucleonics, Inc., Fairfield, N.J.

[21] Appl. No.: 430,759

[22] Filed: Sep. 30, 1982

Related U.S. Application Data

[63] Continuation-in-part of Ser. No. 312,677, Oct. 19, 1981, abandoned.

[51] Int. Cl.$^3$ .............................................. B67D 5/52
[52] U.S. Cl. ................................. 73/863.32; 222/137; 422/100
[58] Field of Search ........... 73/863.32, 864.01, 864.11, 73/864.13, 864.16, 864.17, 864.18; 422/100; 222/135, 136, 137

[56] References Cited

U.S. PATENT DOCUMENTS 3,687,175 8/1972 Babey ............................... 73/863.32
3,837,534 9/1974 Natelson ............................. 222/137
4,106,911 8/1978 Marcelli .......................... 73/863.32

Primary Examiner—S. Clement Swisher
Attorney, Agent, or Firm—Robert Scobey

[57] ABSTRACT

An assembly for loading and dispensing varying amounts of fluid from multiple syringes is disclosed. A body member having spaced-apart surfaces $A_o$ and $B_o$ coacts with a handle member having spaced-apart surfaces $A_1$ and $B_1$ ($A_1$ and $B_1$ are either fixedly spaced or variably spaced) parallel to the surfaces $A_o$ and $B_o$. The handle member is mounted for relative reciprocal movement with respect to the body member in a direction $D_o$ the same as a vector perpendicular to the surfaces $A_o$ and $B_o$. A plurality of syringe actuators each associated with an individual one of the syringes is included, and they are mounted for relative movement with respect to the body member. Each syringe actuator has actuating surfaces for respective contact with the surfaces $A_o$ and $B_o$ on the body member and $A_1$ and $B_1$ on the handle member.

9 Claims, 9 Drawing Figures

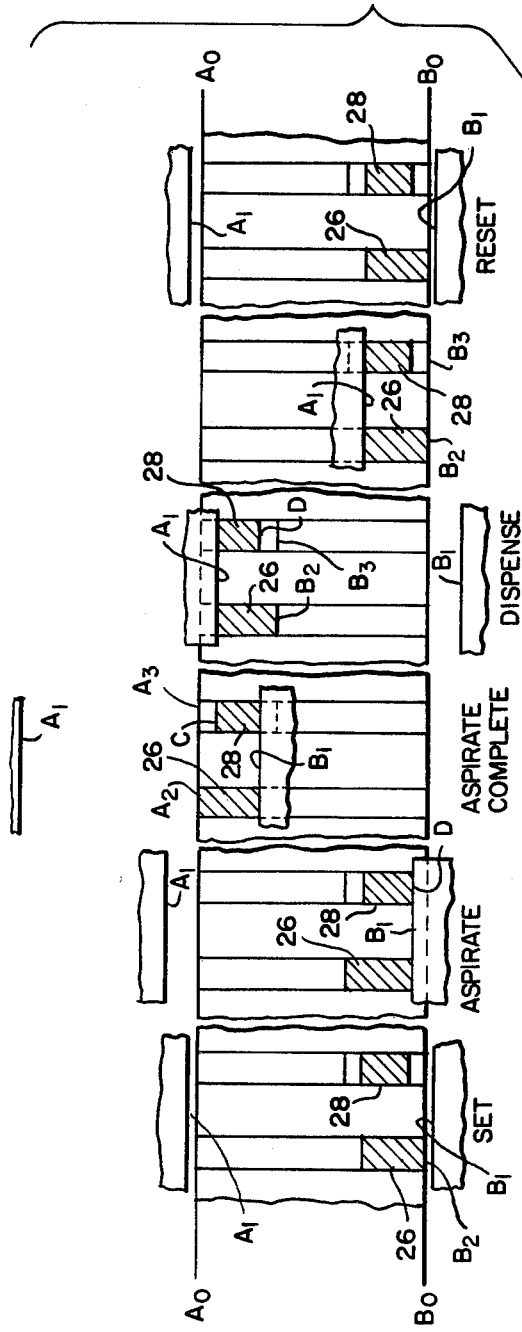
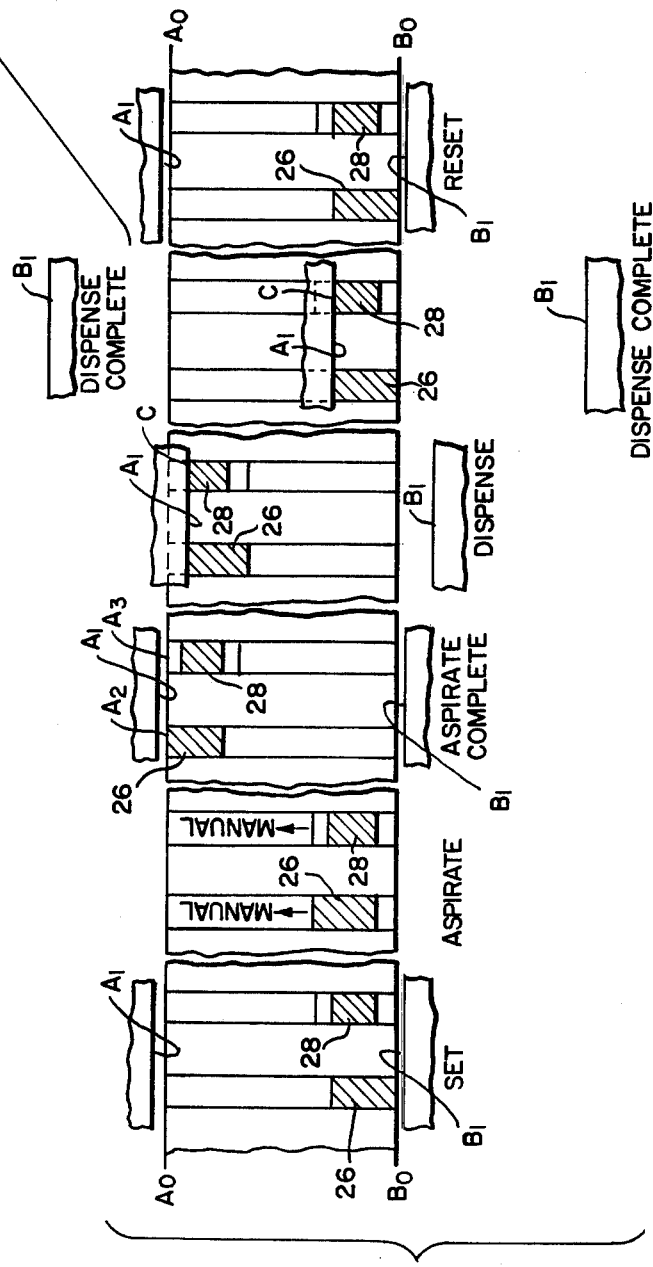
FIG. 2.
FIG. 3.

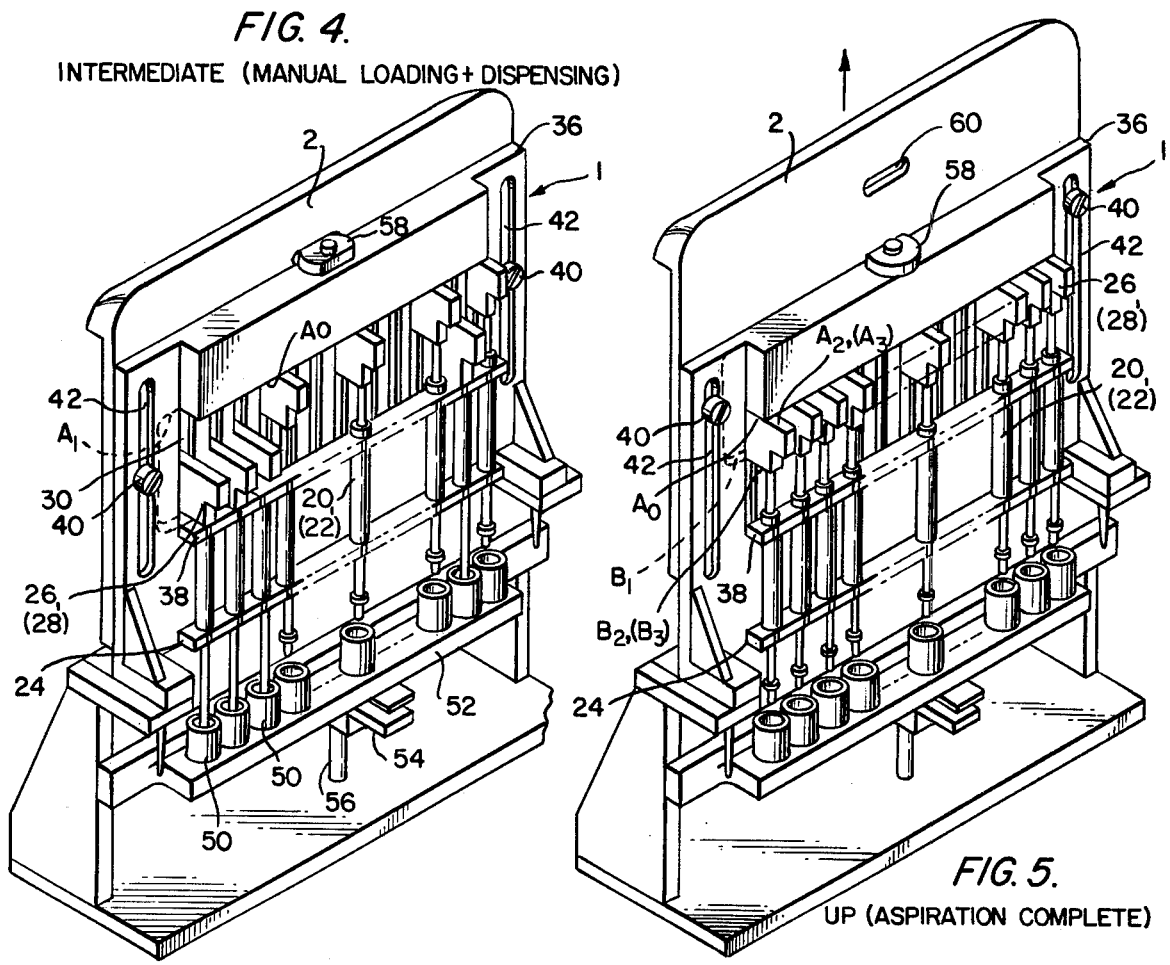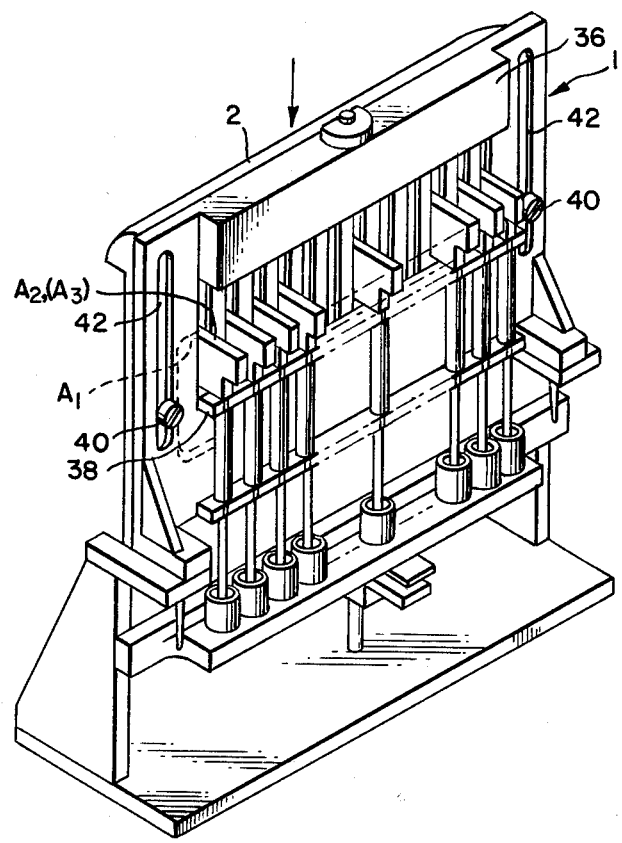

FLUID LOADING AND DISPENSING DEVICE

CROSS REFERENCE TO RELATED APPLICATION

This application is a Continuation-In-Part of copending application Ser. No. 06/312,677 filed Oct. 19, 1981, now abandoned.

BACKGROUND AND BRIEF DESCRIPTION OF THE INVENTION

This invention relates to assemblies for loading and dispensing varying amounts of fluid from multiple syringes.

Natelson U.S. Pat. No. 3,837,534 which issued Sept. 24, 1974 discloses a fluid dispenser capable of dispensing a plurality of fluids from separate containers, with the volume dispensed from each container being independently adjustable over a range. That dispenser is adapted for actuation by a motor driven cam assembly, and is thus rather complex and not suited for manual dispensing of fluid.

The present invention is directed to an assembly for loading and dispensing varying amounts of fluid, in which plural syringes capable of loading and dispensing varying amounts of fluid may be actuated either individually or together as a group.

A presently preferred embodiment of the invention utilizes a body member that has spaced-apart surfaces $A_0$ and $B_0$, acting with a handle member having spaced-apart surfaces $A_1$ and $B_1$ parallel to the surfaces $A_0$ and $B_0$. The handle member is mounted for relative reciprocal movement with respect to the body member in a direction $D_0$ the same as a vector perpendicular to the surfaces $A_0$ and $B_0$. A plurality of syringe actuators are utilized, each associated with an individual one of the syringes and mounted for relative movement with respect to the body member. Each syringe actuator has actuating surfaces for respective contact with the surfaces $A_0$, $B_0$, $A_1$, and $B_1$.

In an intermediate position of the handle member with respect to the body member, the syringe actuators may be moved individually and by hand to load and dispense fluid from the syringes. Alternatively, the handle member may be moved relative to the body member, moving the syringe actuators as a group so as to load and dispense fluids from and to a number of containers with just one cycle of loading movement and dispensing movement of the handle member. Actuating surfaces on the syringe actuators in different planes provide for lost motion movement of the handle member to achieve the loading and dispensing of varying amounts of fluid from the syringes by virtue of unequal syringe piston movements.

The handle member may be an integral piece, in which case the surfaces $A_1$ and $B_1$ move together and are spaced apart by a fixed distance. Alternatively, the handle member may be made of separate handle pieces, in which case the surfaces $A_1$ and $B_1$ may move independently and be spaced-apart by varying distances.

The invention will be more completely understood by reference to the following detailed description.

BRIEF DESCRIPTION OF THE DRAWINGS

FIG. 2 schematically illustrates the movement of syringe actuators, when moved in common by suitable movement of the handle member in the system of FIG. 1.

FIG. 3 schematically illustrates the movement of the syringe actuators, when they are moved individually by hand.

FIGS. 4 to 6 are perspective views of an assembly of the type of FIG. 1, in varying conditions of handle position, namely, with FIG. 4 illustrating an intermediate handle position in which the syringe actuators may be moved by hand, with FIG. 5 illustrating an up position of the handle member and FIG. 6 illustrating a down position of the handle member, both useful in showing the common movement of the syringe actuators by movement of the handle member.

DETAILED DESCRIPTION

Figure 1:
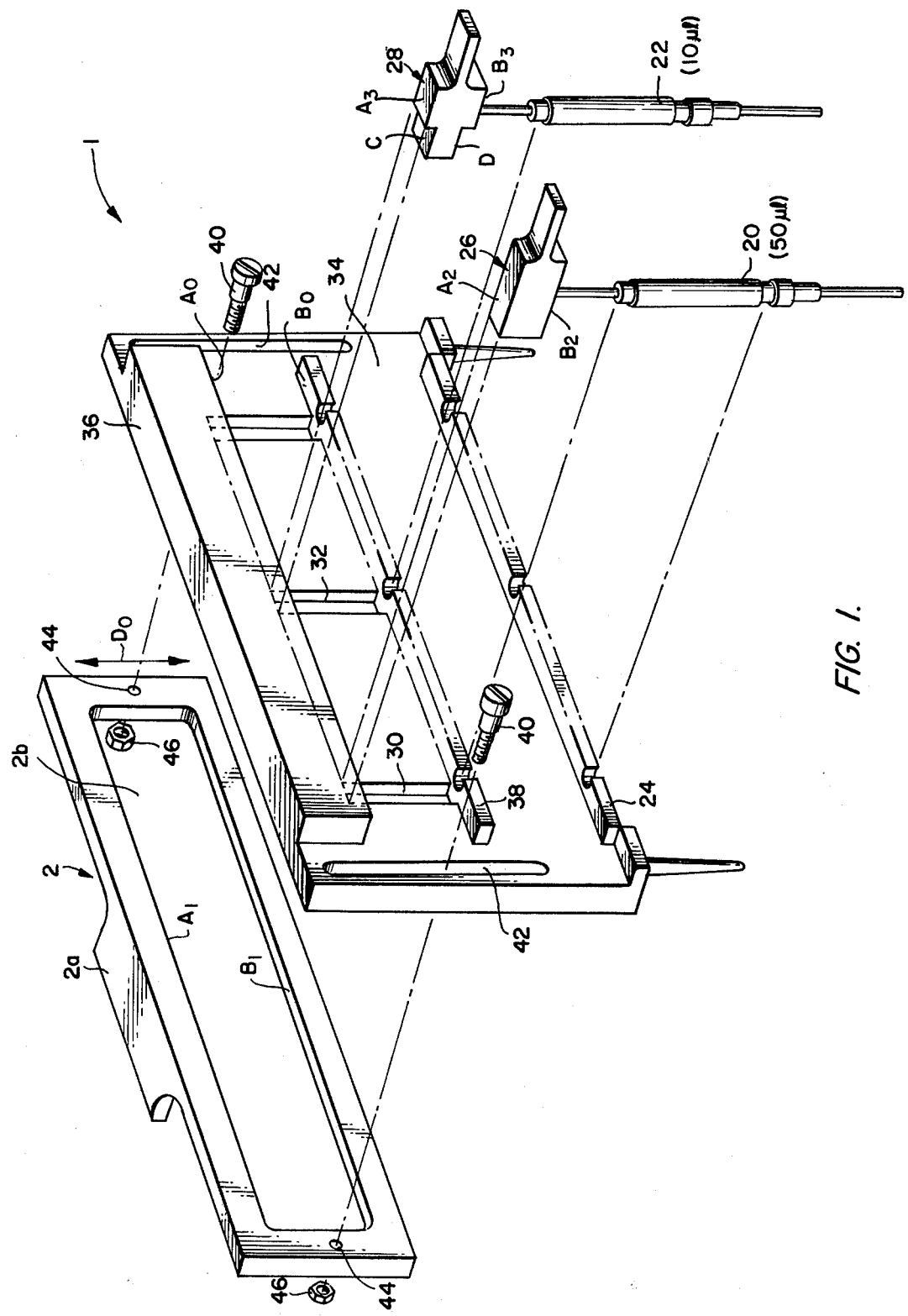
FIG. 1 is an exploded view of a loading and dispensing assembly embodying the present invention.

Referring to FIG. 1, an assembly is shown, in exploded form, suitable for loading and dispensing varying amounts of fluid from multiple syringes, only two of which (syringes 20 and 22) have been shown as representative. As an example, the syringe 20 is a 50 microliter syringe, with a displacement of 0.82 inch, while the syringe 22 is a 10 microliter syringe, with a displacement of 0.74 inch. The syringes are mounted on a mounting plate 24 that forms a part of a body member 1. The syringes are actuated by syringe actuators 26 and 28, which are adapted to slide in grooves 30 and 32 formed in a back plate 34, all forming a part of the body member 1. The grooves 30 and 32 are bounded at the top and bottom thereof by stops 36 and 38, which also form a part of the body member 1. The stop 36 has a lower surface $A_0$, while the stop 38 has an upper surface $B_0$. These surfaces are spaced-apart on the body member, and limit the vertical movement of the syringe actuators 26 and 28 sliding within the grooves 30 and 32. In particular, the syringe actuators 26 and 28 include actuating surfaces that contact the spaced-apart stop surfaces $A_0$ and $B_0$ on the body member 1 at the extreme positions of the syringe actuators 26 and 28. Thus the syringe actuator 26 includes an upper actuating surface $A_2$ and a lower actuating surface $B_2$ that respectively contact the surfaces $A_0$ and $B_0$. Likewise, the syringe actuator 28 includes an upper actuating surface $A_3$ and a lower actuating surface $B_3$ which respectively contact the stop surfaces $A_0$ and $B_0$ on the body member 1.

Additionally included as part of the assembly is a unitary handle member 2, which includes a handle portion $2_a$ and which is otherwise generally rectangularly shaped, with a rectangular opening $2_b$ therein that defines stop surfaces $A_1$ and $B_1$ which are opposed from each other by a fixed distance. The handle member 2 is mounted for relative reciprocal movement with respect to the body member 1, for example, by virtue of screws 40 which pass through slots 42 on opposed sides of the body member 1 and through holes 44 in the handle member 2, to be held in place by nuts 46.

It will be noted from FIG. 1 that the stop surfaces $A_0$ and $A_1$, $B_0$ and $B_1$ respectively on the body and handle members are parallel to each other, and the handle motion of the handle member 2 is in the same direction as a vector $D_0$ perpendicular to the two body member surfaces $A_0$ and $B_0$. The fixed distance between the surfaces $A_1$ and $B_1$ on the handle member 2 is advantageously slightly greater than the distance between the surfaces $A_0$ and $B_0$ on the body member, although theoretically these two distances could be equal.

The surfaces $A_1$ and $B_1$ on the handle member are adapted to make contact with the actuating surfaces of the syringe actuators 26 and 28. Specifically, the surfaces $A_2$ and $B_2$ of the syringe actuator 26 may be contacted respectively by the surfaces $A_1$ and $B_1$ of the handle member 2. Likewise, the surfaces C and D of the syringe actuator 28 may be contacted respectively by the surfaces $A_1$ and $B_1$ of the handle member.

The movement of the syringe actuators 26 and 28 in a completed assembly is best considered with respect to FIGS. 2 and 3. FIG. 2 schematically shows the coordinated movement of the surfaces $A_1$ and $B_1$ of the handle member 2, as well as the movement of the syringe actuators 26 and 28, during movement of the handle to actuate all the syringes, as a group. FIG. 3, on the other hand, schematically shows the movement of the syringe actuators 26 and 28 when they are actuated individually by hand.

Referring to FIG. 2, the left-most portion of the figure shows the relative positions of all members of the assembly in the "set" position, just prior to the movement of the handle member 2 upwardly to aspirate liquid from containers (shown in FIGS. 4 to 6) into the syringes 20 and 22. Movement of the handle member 2 first causes the surface $B_1$ to contact the surface $B_2$ of the syringe actuator 26 and to raise that actuator to the position shown in the "aspirate" portion of FIG. 2 when that same surface $B_1$ just makes contact with the lower surface D on the syringe actuator 28. Further upward movement of the handle member 2, to aspiration completion, is shown in the "aspirate complete" portion of FIG. 2. At this point, further upward movement is limited by the engagement of the upper surfaces $A_2$ and $A_3$ of the syringe actuators 26 and 28 with the stop surface $A_0$ on the body member. Because of the different actuating surfaces employed on the syringe actuators 26 and 28, which actuating surfaces lie in plural planes, the two syringes are caused to aspirate differing amounts of fluid.

Next a "dispense" operation is commenced, as shown by the "dispense" portion of FIG. 2. The handle member 2 is moved downwardly, until the surface $A_1$ thereon engages the actuator surface $A_2$ on the syringe actuator 26, moving that syringe actuator downwardly until the surface C on the syringe actuator 28 is engaged by the handle surface $A_1$. Completion of dispensing is as shown in the "dispense complete" portion of FIG. 2, when the surface $A_1$ has moved downwardly as far as it can, limited by engagement of the lower surfaces $B_2$ and $B_3$ with the lower stop surface $B_0$ on the body member 1.

Thereafter, upward movement of the handle member 2 to the "reset" position, as shown at the right in FIG. 2 completes the cycle. In this position, the handle member is the same as in the "set" position at the left-hand portion of FIG. 2.

FIG. 3 shows the action for individual aspirating and dispensing of the syringes. The handle member 2, with its surfaces $A_1$ and $B_1$, is in the "set" position as shown at the left-hand portion of FIG. 3. This is an "intermediate" position of the handle member, permitting the syringe actuators 26 and 28 to be moved upwardly and downwardly and limited only by engagement of the respective actuating surfaces $A_2/A_3$ and $B_2/B_3$ respectively with $A_0$ and $B_0$. As shown in the "aspirate" portion of FIG. 3, the syringe actuators 26 and 28 are moved upwardly by hand to complete an aspiration cycle, as shown in the "aspirate complete" portion of FIG. 3. In this latter position of the syringe actuators, their upward movement is limited by the stop surface $A_0$ on the body member 1, which contacts the actuating surfaces $A_2$ and $A_3$.

Dispensing following aspiration may be done by hand or, alternatively, in common as to all syringes by suitable downward movement of the handle member 2. Such downward movement of the handle member 2 is shown in FIG. 3 by the last three portions of FIG. 3 (on the right) labeled "dispense", "dispense complete", and "reset". It will be noted from a comparison of FIGS. 2 and 3, that these last three conditions are the same for FIGS. 2 and 3.

FIGS. 4 to 6 are perspective views of a completed assembly, of the type of FIG. 1, shown in the various conditions of the handle member 2, namely, an intermediate position of the handle member (FIG. 4), and "up" position of that handle member (FIG. 5) and a "down" position of that handle member (FIG. 6). In the "intermediate" position of the handle member, as shown in FIG. 4, the surfaces $A_0$ and $A_1$ of the body and handle members are adjacent each other, as are the surfaces $B_0$ and $B_1$. This intermediate position of the handle member permits the syringe actuators 26 and 28 to move freely within the grooves 30 and 32 in the body member for manual aspirating and dispensing of the syringes with respect to containers 50 carried by a carrier 52, as desired, or manual aspirating with group dispensing, all as described above. The container carrier 52 is vertically adjustable by clamp 54 vertically positionable on post 56. If desired, the body member may include a latch 58 at the top thereof which passes through a slot 60 in the top of the handle member to fix the handle member with respect to the body member so that the two may not move relatively (as in FIG. 4). For relative movement of the handle and stop members, the latch is pivoted so that it no longer engages the slot in the handle member, permitting that handle member to move relatively with respect to the body member. Such is the condition shown in FIGS. 5 and 6. Alternatively, a detent mechanism may be employed, so that the handle member, when moved relatively to the body member, is maintained in its intermediate, up, and down positions, and some degree of force must be used to move the handle member away from these positions.

Figure 7:
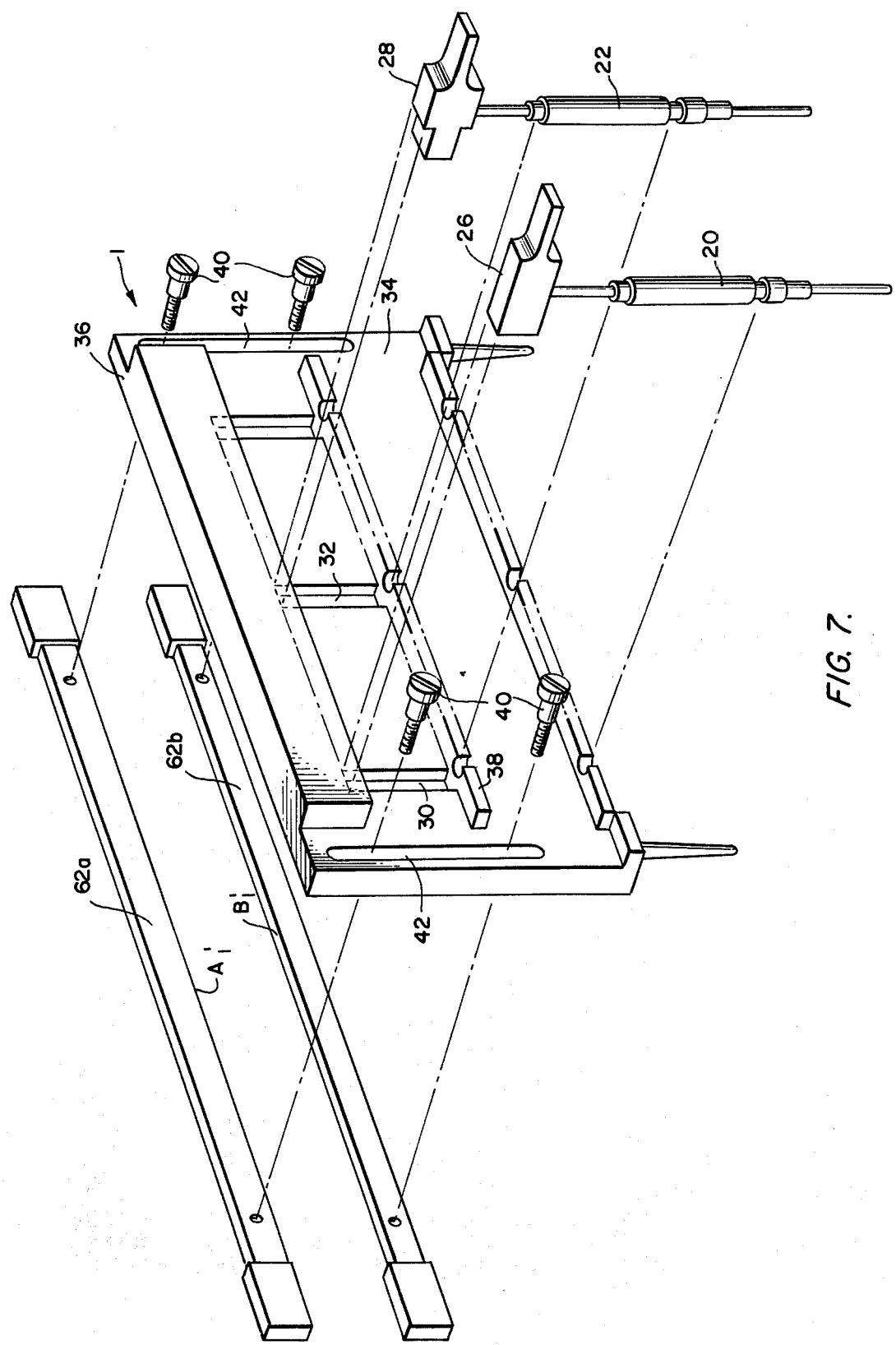
FIG. 7 is an exploded view of another loading and dispensing assembly presently preferred and embodying the present invention.
Figure 8:
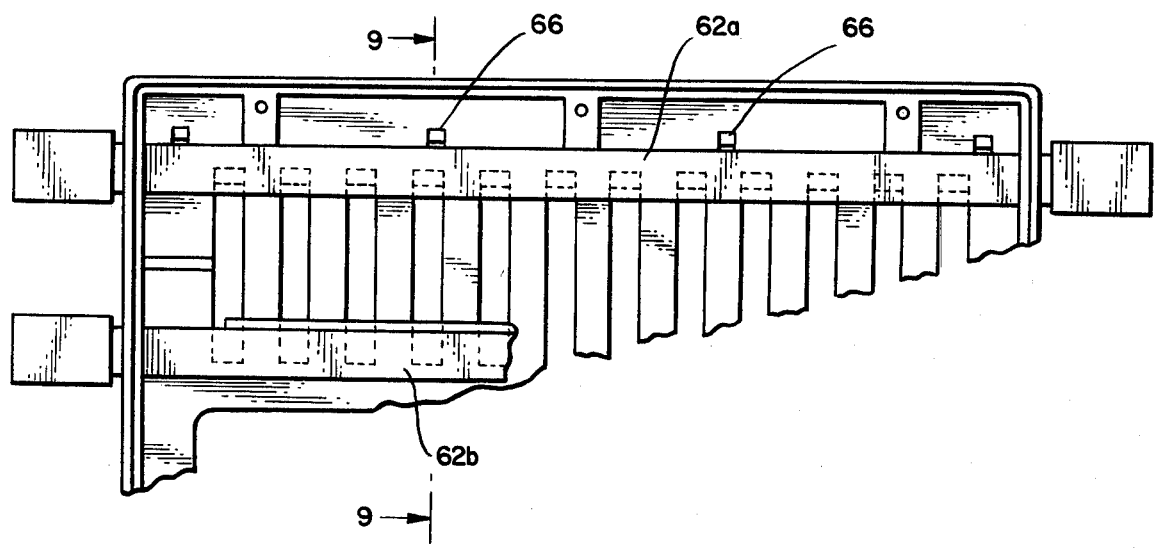
FIG. 8 is a rear view of part of the assembly of FIG. 7.
Figure 9:
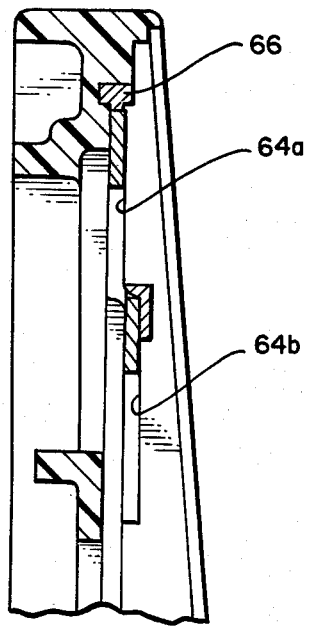
FIG. 9 is a sectional view, taken along the section 9—9 in FIG. 8.

FIGS. 7-9 show an alternative system, similar to that of FIGS. 1-6, and presently preferred, in which the handle member comprises two separate handle pieces 62a and 62b providing surfaces $A_1'$ and $B_1'$ corresponding to the surfaces $A_1$ and $B_1$ in FIG. 1. In this case, however, the handle pieces are independently movable, so that the surfaces $A_1'$ and $B_1'$ are not spaced by a fixed distance. The syringe actuators 26, 28 are lowered as a group by handle piece 62a and are raised as a group by handle piece 62b. The handle pieces ride in offset grooves 64a and 64b (FIG. 9), the ends of which may limit the vertical movement of the handle pieces. The upper handle piece 62a may be of metal and held in its uppermost position by magnets 66 (FIGS. 8 and 9). Otherwise, the operation is as explained above for FIGS. 1-6.

It will be noted, from the description above, that simple but highly effective assemblies for aspirating and dispensing varying amounts of fluid into and from multiple syringes have been disclosed. The presently preferred embodiments are subject to modification. For example, while straight-line arrays of syringes have been illustrated, a curved array, such as circular, is possible. As another example, the syringe actuator 28 is shown formed with four actuating surfaces; the same results could be obtained with three surfaces. Accordingly, the invention should be taken to be defined by the following claims.

I claim:

1. An assembly for loading and dispensing varying amounts of fluid from multiple syringes comprising a body member having spaced-apart surfaces $A_0$ and $B_0$, a handle member having spaced-apart surfaces $A_1$ and $B_1$ parallel to said surfaces $A_0$ and $B_0$ and mounted for relative reciprocal movement with respect to said body member in a direction $D_0$ the same as a vector perpendicular to said surfaces $A_0$ and $B_0$, and a plurality of syringe actuators each associated with an individual one of said syringes and mounted for relative movement with respect to said body member, each syringe actuator having actuating surfaces for respective contact with said surfaces $A_0$, $B_0$, $A_1$ and $B_1$.

2. An assembly as in claim 1, in which said surfaces $A_0$ and $B_0$ are spaced-apart by a fixed distance.

3. An assembly as in claim 2, in which said handle member is relatively movable between positions in which:

(a) the surfaces $A_0$ and $A_1$ are adjacent each other, and the surfaces $B_0$ and $B_1$ are adjacent each other, for manual actuation of said syringe actuators:

(b) the surfaces $A_0$ and $B_1$ are adjacent each other, representing completion of ganged movement of said syringe actuators in aspirating fluid into said syringes;

(c) the surfaces $A_1$ and $B_0$ are adjacent each other, representing completion of ganged movement of said syringe actuators in dispensing fluid from said syringes.

4. An assembly as in claim 3, in which said surfaces $A_0$ and $B_0$ are spaced-apart by slightly less than the distance between said surfaces $A_1$ and $B_1$.

5. An assembly as in claim 1, in which said handle member is formed from separate handle pieces independently movable, one handle piece having said surface $A_1$ and the other having said surface $B_1$.

6. An assembly as in claim 5, in which one handle piece moves all said syringe actuators in one direction for aspiration of fluid into said syringes, and the other of said handle pieces moves all said syringe actuators in an opposite direction for dispensing fluid from said syringes, and in which said handle pieces may be spaced-apart by a sufficient distance to permit said syringe actuators to be moved individually and manually.

7. An assembly as in claim 3 or 6, in which said actuating surfaces lie in plural planes.

8. An assembly as in claim 7, in which there are at least two of said plural planes.

9. An assembly as in claim 7, in which there are more than two of said plural planes.

* * * * *